United States Patent [19]

Oberst et al.

[11] Patent Number: 5,424,189

[45] Date of Patent: Jun. 13, 1995

[54] BOVINE RESPIRATORY SYNCYTIAL VIRUS DETECTION AND PRIMERS

[75] Inventors: Richard D. Oberst, Manhattan; Michael P. Hays, Leonardville, both of Kans.

[73] Assignee: Kansas State University Research Foundation, Manhattan, Kans.

[21] Appl. No.: 29,327

[22] Filed: Mar. 5, 1993

[51] Int. Cl.⁶ .................. C12Q 1/68; C12P 19/34; C07H 21/00
[52] U.S. Cl. ........................... 435/6; 435/91.1; 435/91.2; 536/24.3; 536/24.32; 536/24.33
[58] Field of Search .............. 435/6, 91, 5, 91.1, 435/91.2, ; 536/24.3, 24.33, 2.43, 24.32; 935/78

[56] References Cited

PUBLICATIONS

Lerch et al. Virology 181: 118–131 (1991).
Pharmacia P-L Biochemicals 1991/1992 Catalog, p. 10.17, Piscataway, New Jersey, U.S.A.
Baker et al., "Serologic Studies of Bovine Respiratory Syncytial Virus in Minnesota Cattle," *Am. J. Vet. Res.* 46:891–892.
Beaucage et al., "Deoxynucleoside Phosphoramidites—A New Class of Key Intermediates for Deoxypolynucleotide Synthesis," *Tetrahedron Letters*, 22:1859–62 (1981).
Bilofsky, et al., "The GenBank Genetic Sequence Data Bank," *Nucl. Acids Res.* 16:1861–63 (1988).
Chomczynski, et al., "Single-Step Method of RNA Isolation by Acid Guanidinium Thiocyanate-Phenol-Chloroform Extraction," *Anal. Biochem.* 162:156–159 (1987).
Collins, et al., "Prevalence and Specificity of Antibodies to Bovine Respiratory Syncytial Virus in Sera from Feedlot and Range Cattle," *Am. J. Vet. Res.* 49:1316–19 (1988).
Cubie, et al., "Detection of Respiratory Syncytial Virus Antigen and Nucleic Acid in Clinical Specimens Using Synthetic Oligonucleotides," *J. Virol. Methods* 34:27–35 (1991).

Edwards, et al., "Respiratory Syncytial Virus Diagnosis," *Vet. Rec.* 114:101 (1984).
Himes et al., "Bovine Respiratory Syncytial Virus Fusion Protein Gene: Sequence Analysis of cDNA and Expression Using a Baculovirus Vector," *J. Gen. Virol.* 73:1563–67 (1992).
Lehmkuhl, et al., "Characterization and Identification of a Bovine Respiratory Syncytial Virus Isolated From Young Calves," *Am. J. Vet. Res.* 40:124–6 (1979).
Lerch, et al., "Nucleotide Sequence Analysis of the Bovine Respiratory Syncytial Virus Fusion Protein mRNA and Expression from a Recombinant Vaccinia Virus," *Virol.* 181:118–31 (1991).
Mullis et al., "Specific Synthesis of DNA in Vitro via a Polymerase-Catalyzed Chain Reaction," *Meth. in Enzymol.*, 155:335–350 (1987).
Okamoto, et al., "Genomic Sequences of Respiratory Syncytial Virus in Otitis Media With Effusion," *The Lancet* 338:1025–26 (1992).
Ou, et al., "DNA Amplification for Direct Detection of HIV-1 in DNA of Peripheral Blood Mononuclear Cells," *Science*, 239:295–97 (1988).
Paton, et al., "Rapid Detection of Respiratory Syncytial Virus in Nasopharyngeal Aspirates by Reverse Transcription and Polymerase Chain Reaction Amplification," *J. Clin. Microbiol.* 30:901–04 (1992).
Rothbarth, et al., "Reliability of Two New Test Kits for Rapid Diagnosis of Respiratory Syncytial Virus Infection," *J. Clin. Microbiol.* 29:824–826 (1991).
Saiki, et al., "Primer-Directed Enzymatic Amplification of DNA with a Thermostable DNA Polymerase," *Science*, 239:487–91 (1988).

(List continued on next page.)

*Primary Examiner*—Margaret Parr
*Assistant Examiner*—David Schreiber
*Attorney, Agent, or Firm*—Tilton, Fallon, Lungmus & Chestnut

[57] ABSTRACT

The use of specific primers and a probe in a reverse transcriptase-polymerase chain reaction provides a method for specifically identifying bovine respiratory syncytial virus in cattle.

4 Claims, No Drawings

OTHER PUBLICATIONS

Smith, et al., "Isolation, Characterization, and Pathogenicity Studies of a Bovine Respiratory Syncytial Virus," *Arch. Virol.* 47:237–47 (1975).

Sullender, et al., "Genetic Diversity of the Attachment Protein of Subgroup B Respiratory Syncytial Viruses," *J. Virol.* 65:5425–34 (1991).

Sullender et al., "Synthetic Oligonucleotide Probes Differentiate Respiratory Syncytial Virus Subgroups in a Nucleic Acid Hybridization Assay", *J. Clin. Microbiol.* 29:1255–57 (1991).

Takimoto, et al., "Comparison of Enzyme-Linked Immunosorbent Assay, Indirect Immunofluorescence Assay, and Virus Isolation for Detection of Respiratory Viruses in Nasopharyngeal Secretions," *J. Clin. Microbiol.* 29:470–74 (1991).

Walravens, et al., "Sequence Comparison between the Fusion Protein of Human and Bovine Respiratory Syncytial Viruses," *J. Gen. Virol.* 71:3009–14 (1990).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

TTACCACACC CCTCAGTACA 20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:2:

CATTGTGTCA CAGAACACTC 20

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:3:

GTGGTCAAAG AAGAGGTCAT 20

BOVINE RESPIRATORY SYNCYTIAL VIRUS DETECTION AND PRIMERS

FIELD OF THE INVENTION

The field of this invention is the detection of the bovine respiratory syncytial virus (BRSV). More particularly, the invention is concerned with the identification of bovine respiratory syncytial virus nucleic acid sequences that can be used to probe for bovine specific respiratory syncytial infection. This invention provides specific DNA primers, probe and describes their use in an amplification assay for bovine respiratory syncytial virus.

BACKGROUND OF THE INVENTION

Detection of DNA in specimens comprising body fluids or tissues can be difficult because of the small quantity of DNA present or because of the presence in the specimen of other interfering materials, including DNA from a different source. These limitations may be overcome by employing an analytic method referred to as the polymerase chain reaction (PCR) technique. By this technique, selective enrichment of a specific DNA sequence can be achieved by exponential amplification of the target sequence. Mullis, et al., Met. Enzymol., 155, 335 (1987).

To facilitate PCR amplification, pairs of oligonucleotide primers may be employed as described in U.S. Pat. No. 4,683,202 (hereby incorporated by reference). The primers are designated to hybridize with sequences that flank the target DNA. Following in vitro amplification, the amplified target sequence is detected by a hybridizing probe. For example, this analytical procedure has been used for the direct detection of HIV-1 as described by Ou, et al., Science, 238, 295-97 (1988). The amplification cycles are facilitated by using a polymerase which is thermally stable in incubations up to 95 degrees centigrade, as described by Saiki, et al., Science, 239, 487-91 (1988).

Bovine respiratory syncytial virus (BRSV), a pneumovirus in the family Parayxoviridae, is an important cause of acute respiratory disease in postweaning calves and feedlot cattle in the United States. In Europe, BRSV infection is considered to be one of the most significant causes of bovine respiratory disease. Although most infections are not apparent, the high prevalence of seropositive cattle in the United States indicated that infection rates are high.

A major problem with establishing a more accurate understanding of BRSV's role in bovine respiratory disease is the difficulty associated with rapidly and accurately identifying the presence of the virus. Successful laboratory diagnosis of BRSV is generally based on one of three criteria: (1) virus isolation, (2) identifying BRSV antigens in suspected tissue, or (3) indications of BRSV seroconversion. However, the lack of standardized reagents, the high prevalence of cattle with antibody titers to BRSV (60-80% seropositive) and the need for skilled personnel to process and interpret fluorescent antibody results have hindered development of routine diagnostic test. Similarly, successful virus isolations from typical clinical cases of BRSV infection are often unsuccessful and can take from 11-21 days because of the late appearance of any noticeable cytopathic effect. Because of these difficulties, direct isolation of BRSV is not recommended as a routine procedure. See Edwards et al., Respiratory Syncytial Virus Diagnosis, Vet. Res. 114:101 (1984).

Human respiratory syncytial (HRSV) is the most important cause of respiratory disease in infants and young children, and the rapid detection of HRSV antigens in clinical specimens has been useful in diagnosing and limiting the nosocomial spread of HRSV associated bronchiolitis and pneumonia. Similarly, synthetic oligonucleotide probes have been used for in situ hybridizations to identify HRSV in nasopharyngeal secretions (Cubie et. al. Detection of Respiratory Syncytial Virus Antigen and Nucleic Acid in Clinical Specimens using Synthetic Oligonucleotides, J. Virol. Methods. 34: 27-35 (1991), and cDNA probes and synthetic oligonucleotides have been used to differentiate HRSV subgroups (Sullender et al., Genetic Diversity of the Attachment Protein of Subgroup B Respiratory Syncytial Viruses, J. Viro. 65:5425-34 (1991), Sullender et al.,Synthetic Oligonucleotide Probes Differentiate Respiratory Syncytial Virus Subgroups in a Nucleic Acid Hybridization Assay, J. Clin. Microbiol. 29:1255-57 (1991). Additionally, reverse transcription and polymerase chain reactions have been combined to amplify and detect low levels of HRSV mRNA from nasopharyngeal aspirates (Paton et al., Rapid Detection of Respiratory Synbctial Virus in Nasopharyngeal Aspirates by Reverse Transcription and Polymerase Chain Reaction Amplification, J. Clin. Microbiol. 30:901-904 (1992) and otitis media effusion (Okamoto et al., Genetic Sequences of Respiratory Syncyntial Virus in Otitis Media with Effusion, Lancet 338;1025-26 (1992).

With this background in mind a method for amplifying, detecting and differentiating BRSV fusion (F) protein mRNA from HRSV mRNA using RT-PCR and oligonucleotides probes was developed.

SUMMARY OF THE INVENTION

The present invention provides a method for specifically detecting respiratory syncytial virus in cattle. The method involves a BRSV-specific negative sense oligonucleotide primer to synthesize cDNA from BRSV fusion protein mRNA template and another BRSV-specific positive oligonucleotide primer upstream from the negative sense primer for PCR amplification. In the presence of a BRSV mRNA template of BRSV strains isolated throughout the United States at different times, the BRSV RT-PCR assay amplified products (381 base pair) were BRSV-specific as demonstrated by hybridization with a positive sense oligonucleotide probes complementary to internal sequences.

More specifically the present invention provides a method of detecting BRSV infection in cattle by primer directed amplification wherein a sample of nucleic acid from the respiratory tract of a cow is amplified with dual primers consisting of the following two single strand oligonucleotides: TTACCACACCCCTCAGTACA (Sequence Id. no. 1) and (CATTGTGTCACAGAACACTC) Sequence Id. no. 2, and following said amplification, hybridizing a single strand oligonucleotide probe (GTGGTCAAAGAAGAGGTCAT) Sequence Id. no. 3 to the amplification product and detecting the hybridized probe, wherein A is adenosine, T is thymidine, G is guanosine, and C is cytosine, the sequence being in the 5' to 3' orientation. More specifically, synthetic oligonucleotides useful in detecting BRSV infection in cattle represented by the DNA sequences TTACCACACCCCTCAGTACA (Sequence Id. no. 1), CATTGTGTCACAGAACACTC (Sequence Id. no. 2) GTGGTCAAAGAAGAGGT-CAT (Sequence Id. no. 3), wherein A is adenosine, T is thymidine, G is guanosine, and C is cytosine, the sequence being in the 5' to 3' orientation.

DETAILED DESCRIPTION OF THE INVENTION

The present invention provides a method for detecting BRSV in cell culture using reverse transcription and polymerase chain reaction to amplify small amounts of BRSV mRNA. DNA-DNA hybridizations can then be used to confirm the specificity of the amplified product as being BRSV.

This technique provides a sensitive and specific method for rapidly and accurately detecting the presence of BRSV. The ability to demonstrate the presence of the F protein mRNA in cells infected with BRSV by RT-PCR and then confirm the specificity of the amplification by DNA hybridizations has significant implications in clarifying BRSV's role in bovine respiratory disease. In practice it is envisioned that direct testing of cattle nasopharyngeal aspirates, respiratory secretions, or lung tissues for the presence of BRSV may be conducted.

The method of this invention uses synthetic oligonucleotide sequences as primers and probes. These sequences can be prepared by well known chemical procedures, and commercially available DNA synthesizers can also be used. For example, the required sequence can be prepared by the synthesis method described by Beaucage, et al., *Tetrahedron letters,* 22: 1859-62 (1981). Another method for the synthesis of oligonucleotide on the solid support is described in U.S. Pat. No. 4,458,066. Automated DNA synthesis apparatus can be used such as the DNA synthesizer sold by Applied Biosystems.

Oligonucleotide sequences required for practicing the method of this invention comprise primer sequences and probe sequences or the inversions of the probe and probe sequences or the inversions of the probe sequences. The single strand oligonucleotide are represented by the standard letter abbreviations in which the nucleotide are designate as follows: A for adenosine, T for thymidine, G for guanosine, and C for cytosine. These strands are represented in a standard 5' prime to 3' prime orientation.

Primer Sequences

BRSV (+) sense primer: 5' TTACCACACCCCT-CAGTACA Sequence Id. no. 1
BRSV(−) sense primer: 5' CATTGTGT-CACAGAACACTC Sequence Id. no. 2.

Probe Sequence

BRSV oligonucleotide probe: 5'GTGGTCAAAGAAGAGGTCAT Sequence Id. no. 3.

Primer Selection

The primer sequences can be used in the genetic amplification of the BRSV mRNA. The primers are designed to hybridize with highly conserved regions of BRSV fusion protein mRNA. These primers are capable of effectively hybridizing and serving as primers for the thermostable DNA polymerase used in the amplification process. More specifically the primer selection involved the following process.

Sequence data on the fusion protein (F) to BRSV strain RB 94 (Walravens et al.,Sequence Comparison Between the Fusion Protein of Human and Bovine Respiratory Syncytial Viruses, *J. Gen. Virol.* 71:3009-3014 (1990)) and BRSV strain 391-2 (Lerch et al., Nucleotide Sequence Analysis of the Bovine Respiratory Syncytial Virus Fusion Protein mRNA and Expression from a Recombinant Vaccinia Virus, *Virol.* 181:118-31 (1991)) were compared. Either BRSV strain RB 94 or ATCC A51908 or both may be used. The conserved regions were analyzed as potential oligonucleotide primers or internal oligonucleotide probes using software specifically designed for primer selection, NUCIT ™ (Compuright, Washington Grove, Md.).

More specifically, with the aid of the above discussed selection software, a primer pair was selected BRSV (+) sense primer: 5' TTACCACACCCCTCAG-TACA (Sequence Id. no. 1) and BRSV(−) sense primer: 5' CATTGTGTCACAGAACACTC (Sequence Id. no. 2), that would encode a 381 basepair fragment (nt. 741-1123) of the $F_1$ subunit of the BRSV (strain 391-2) F protein mRNA. An internal oligonucleotide was selected as a probe: BRSV 884-903. 5'GTGGTCAAAGAAGAGGTCAT (Sequence Id. no. 3), nt. 884-903 ($T_h$=filter hybridization dissociation temperature of approximately 52° C.).

The oligonucleotide primer pair and 20-mer internal hybridization probe were synthesized using standard phosphoramidite chemistry on a DNA synthesizer (Model 391 PCR-Mate, Applied Biosystems). Oligonucleotides were removed from columns with 100% ammonium hydroxide and heated at 55° C. for eighteen hours to eliminate protective groups, dried under vacuum, and resuspended in 100 microliters of water according to the manufacturer's instructions. Gel filtration on SEPHADEX G-50 columns (Nick Columns, Pharmacia LKB) were used to purify oligonucleotides.

Reverse transcription and PCR amplification of BRSV (strain 375) mRNA with primers selected from sequence information to the F protein of BRSV 391-2 and RB94 resulted in a discrete fragment of approximately 380 base pairs. When BRSV (strain 375) RT-PCR fragment was cloned in pT7 Blue (R) vector (Novagen, Madision, Wis.), transformed into Nova Blue ™ cells (Novagen), and sequenced (f mole ™ DNA Sequencing Sytem, Promega, Madision, Wis.) indicated that the insert was a 381 base pair identical to sequences of BRSV 391-2 (nucleotides 741-1123) described by Lerch et al. (1991).

Viruses

The BRSV strain 375 was the prototype BRSV in the initial testing of the RT-PCR protocol. The virus was a greater than three times plaque purified BRSV strain originally obtained from cattle and is bovine viral diarrhea virus free. The procedure to obtain the BRSV strain 375 is described in Lehmkuhl et al., Characterization and Identification of Bovine Respiratory Syncytial Virus Isolated from Young Calves, *Am. J. Vet. Res.* 40:124-26 (1979). The following reference strains and field strains of BRSV and HRSV were purchased from the American Type Culture Collection (ATCC) or supplied by other organizations as listed: HRSV A-2 strain (ATCC VR-1302); HRSV long Strain (ATCC VR-26); HRSV 9320 strain (ATCC VR-955); BRSV 391-C2 isolated in North Carolina, BRSV NDKS-7 isolated in North Dakota, BRSV 87-14594 isolated in South Dakota, BRSV 1344 isolated in Colorado, BRSV 411-727 isolated in New York, HRSV CH18537 (subgroup B), HRSV WV4843(subgroup B)(C. Kelling, University of Nebraska, Lincoln, Nebr.);(BRSV Strain A51908) (ATCC VR-794) (J. Evermann, Washington Animal Disease Diagnostic Laboratory, Washington State University, Pullman Wash.); BRSV isolated A2 (subgroup A) and B8/60 (subgroup B) (L. Potgieter, University of Tennessee, Knoxville, Tenn.): and HRSV Long Strain-KSU (R. M. Phillips, Kansas State University, Manhattan, Kans.).

Isolation of RNA

Respiratory syncytial virus strains were grown in bovine turbinate (BT), Madin-Darby bovine kidney (MDBK), or HEp-2 cells in modified Eagle's minimum essential medium (MEM) supplemented with 10% fetal calf or horse serum. Viruses were allowed to replicate and form the characteristic syncytia or cytopathic effect (CPE), at which point the RNA was isolated. Chomczynski et al.,Single-Step Method of RNA Isolation by Acid Guanidium Thiocyanate-Phenol-Chloroform Extraction. *Anal. Biochem.* 162:156–159 (1987). Cells in 75cm$^2$ flasks were rinsed with phosphate buffered saline (PBS, pH±0.4), then lysed in 1.0 ml lysis buffer (4M guanidinium isothiocynate, 25 mM sodium citrate, 0.5% sarcosyl, and 0.1 ml 2 mercaptoethanol). To each 500 microliters of lysed cell suspension, 50 microliters of 2M sodium acetate (pH 4.0) was added and mixed with 500 microliters buffered phenol chloroform:isoamyl alcohol mixture (1:1:0.05). After 15 minutes on ice, the mixtures were centrifuged at 14000×g for twenty minutes and the top aqueous phase was removed to a new microcentrifuge tube, mixed with 1.0 ml of 100% ethanol, stored at 70.0° C. for 15–30 minutes, and centrifuged at 14000×g for twenty minutes. The resulting pellets were dissolved in 300 microliters lysis buffer and mixed with 750 microliters 100% ethanol, stored at −70.0° C. for 15–30 minutes, and recentrifuged at 14000×g for 20 minutes. The pellet was washed in 300 microliters 80% ethanol, recentrifuged for five minutes, vacuum dried, and resuspended in DEPC-treated water; then nucleic acid concentration was quantified ($A_{260}$–$A_{280}$).

RT-PCR Protocol

The respiratory syncytial virus mRNA was reverse transcribed to single-stranded cDNA and amplified by PCR as described by the manufacturer (GENEAMP RNA kit, Perkin Elmer Cetus) using a thermal cycler (GENEAMP PCR System 9600, Perkin Elmer Cetus). Two micrograms of total nucleic acid from BRSV-infected cells served as the source of the mRNA template for reverse transcription (RT) and one micromolar of the (−) sense primer. The final volume for the RT reaction was twenty microliters. Incubation time and temperature for RT were 42° C. for three minutes forty-five seconds, 99° C. for one minute and fifteen seconds, and 5° C. for one minute and fifteen seconds. The resulting cDNA was amplified by PCR by adding one micromolar of the (+) sense primer and bringing the final volume for the PCR reaction to 100 microliters as per kit instructions. Initial denaturing was for thirty seconds at 95° C. followed by thirty-five cycles (fifteen seconds at 95° C., fifteen seconds at 60° C.), and 1 cycle (one minute and forty-five seconds at 60° C.).

Electrophoresis and Southern Blotting

Electrophoretic analysis was completed by electrophoresing forty microliters from each RT-PCR reaction on polyacrylamide gels (4% stacking and 15% resolving) in Tris buffer(0.025M Tris pH 8.3; 0.192M glycine) for eighteen hours at sixty volts. The polyacrylamide gels were transferred to paper (Zeta Probe,Bio-Rad, Inc) by electroblotting (Transsblot, Biorad) for two hours at 75 volts in 1X TAE buffer (0.94M Tris-acetate, 0.0011M EDTA, pH 8.0).

Blots were hybridized overnight with the internal 20mer oligonucleotide probe that had been labeled [$\gamma^{32}$P]ATP using T4 polynucleotide kinase. Hybridization buffer consisted of 10% dextran sulfate, 1% SDS, 1M NaCl, and at $T_{hybridization} = T_{denaturation} - 10°$ C. Washes consisted of 2X SSC (twice for five minutes at room temperature and twice for thirty minutes at Th). Membranes were exposed to x-ray at −70° C. using intensifying screens.

In a sampling of other BRSV strains, including BRSV 391-2, RT-PCR with the same primers resulted in the amplification of similar products of approximately 380 base pairs. When BRSV RT-PCR were completed on the RNA from cultures infected with HRSV, no products were evident at approximately 380 base pairs. Reference strains of HRSV group A virus (Long, and A2) that were amplified with the primers resulted in amplified products of approximately 150 base pairs. Amplification and electrophoresis of HRSV group B (subgroup B1 and subgroup B2) resulted in different profiles. Amplification of subgroup B1 isolated (WV4843, B8/60, VR 9320) did not result in major amplification products, whereas amplification of subgroup B2 (CH18537) resulted in primary product of approximately 900 base pairs.

Blotting and hybridization of the HRSV RT-PCR products with the BRSV884-903 oligonucleotide probe (sequence Id. no 3) did not produce a signal from any of the HRSV strains on Southern blots.

This technique provides a sensitive and specific method for rapidly and accurately detecting the presence of BRSV. The ability to demonstrate the presence of the F protein mRNA in cells infected with BRSV by RT-PCR and then confirm the specificity of the amplification by DNA hybridizations has significant implications in clarifying BRSV's role in bovine respiratory disease. In practice it is envisioned that direct testing of cattle nasopharyngeal aspirates, respiratory secretions, or lung tissues for the presence of BRSV may be conducted.

Although the invention has been described in terms of the specific embodiments many modifications and variations of the present invention are possible in light of the teachings. It is, therefore, to be understood that within the scope of the appended claims the invention may be practiced otherwise than as specifically described.

---

We claim:

1. A method to detect Bovine Respiratory Syncytial Virus (BRSV) from infected tissues comprising performing primer specific RNA transcription based amplication and nucleic acid hybridization comprising specifically reverse transcribing a portion of the Bovine Respiratory Syncytial Virus fusion protein messenger ribonucleic acid (BRSV F protein mRNA) is specifically reverse transcribed into DNA and amplifying said DNA with primers consisting of the following two single oligonucleotides having the DNA sequences:
TTACCACACCCCTCAGTACA (Sequence Id. No. 1) and
CATTGTGTCACAGAACACTC (Sequence Id. No. 2), and following said amplification, hybridizing a single strand oligonucleotide probe consisting of the oligonucleotide having the DNA sequence GTGGTCAAAGAAGAGGTCAT (Sequence Id. No. 3) to said amplification product and detecting said hybridized probe, wherein A is adenosine, T is thymidine, G is guanosine, and C is cytosine, the sequence being in the 5' to 3' orientation.

2. A synthetic oligonucleotide used in detecting Bovine Respiratory Syncytial Virus (BRSV) from infected tissues by polymerase chain reaction wherein said oligonucleotide has the DNA sequence consisting of: TTACCACACCCCTCAGTACA (Sequence Id. No. 1), wherein A is adenosine, T is thymidine, G is guanosine, and C is cytosine, the sequence being in the 5' to 3' orientation.

3. A synthetic aligonucleotide used in detecting Bovine Respiratory Syncytial Virus (BRSV) from infected tissues by polymerase chain reaction wherein said oligonucleotide has the DNA sequence consisting of:
CATTGTGTCACAGAACACTC (Sequence Id. No. 2), wherein A is adenosine, T is thymidine, G is guanosine, and C is cytosine, the sequence being in the 5' and 3' orientation.

4. A synthetic oligonucleotide used in detecting Bovine Respiratory Syncytial Virus (BRSV) from infected tissues by polymerase chain reaction wherein the oligonucleotide has the DNA sequence consisting of: GTGGTCAAAGAAGAGGTCAT (Sequence Id. No. 3), wherein A is adenosine, T is thymidine, G is guanosine, and C is cytosine, the sequence being in the 5' to 3' orientation.

* * * * *

UNITED STATES PATENT AND TRADEMARK OFFICE
CERTIFICATE OF CORRECTION

PATENT NO. : 5,424,189
DATED : June 13, 1995
INVENTOR(S) : Oberst et al.

It is certified that error appears in the above-indentified patent and that said Letters Patent is hereby corrected as shown below:

In column 7, lines 48-49, the words "is specifically reverse transcribed" should be deleted.

Signed and Sealed this

Thirty-first Day of October 1995

Attest:

BRUCE LEHMAN

Attesting Officer     Commissioner of Patents and Trademarks